United States Patent [19]
Fergason

[11] Patent Number: 5,519,522
[45] Date of Patent: May 21, 1996

[54] EYE PROTECTION DEVICE FOR WELDING HELMETS AND THE LIKE WITH HOT MIRROR AND INDIUM TIN OXIDE LAYER

[76] Inventor: Jeffrey K. Fergason, 1050 Ringwood Ave., Menlo Park, Calif. 94025

[21] Appl. No.: 105,734

[22] Filed: Aug. 11, 1993

[51] Int. Cl.$^6$ .................... G02F 1/133; B23K 9/32
[52] U.S. Cl. .................... 359/66; 359/53; 359/93; 359/359; 359/590; 219/147
[58] Field of Search .................... 359/53, 36, 63, 359/83, 66, 85, 93, 71, 359, 584, 589, 590; 2/8; 219/147; 250/201.1; 351/44, 49

[56] References Cited

U.S. PATENT DOCUMENTS

| | | | |
|---|---|---|---|
| Re. 29,684 | 6/1978 | Gordon | 359/84 |
| Re. 32,521 | 10/1987 | Fergason | 359/36 |
| 3,245,315 | 4/1966 | Marks et al. | |
| 3,682,528 | 8/1972 | Apfel et al. | 359/389 |
| 3,918,796 | 11/1975 | Fergason | 359/63 |
| 4,039,254 | 8/1977 | Harsch | 359/53 |
| 4,045,125 | 8/1977 | Farges | 359/498 |
| 4,385,806 | 5/1983 | Fergason | 359/39 |
| 4,436,376 | 3/1984 | Fergason | 359/40 |
| 4,504,109 | 3/1985 | Taga et al. | 359/389 |
| 4,507,547 | 3/1985 | Taga et al. | 359/359 |
| 4,540,243 | 9/1985 | Fergason | 359/53 |
| 4,582,396 | 4/1986 | Bos et al. | 359/64 |
| 4,728,173 | 3/1988 | Toth | 359/63 |
| 5,208,688 | 5/1993 | Fergason et al. | 359/53 |
| 5,282,121 | 1/1994 | Bornhorst et al. | 362/294 |
| 5,296,961 | 3/1994 | Trost et al. | 359/359 |

FOREIGN PATENT DOCUMENTS

| | | |
|---|---|---|
| 0157744 | 9/1985 | European Pat. Off. . |
| 9216820 | 10/1992 | WIPO . |
| 9313397 | 7/1993 | WIPO . |
| 9313449 | 7/1993 | WIPO . |

*Primary Examiner*—William L. Sikes
*Assistant Examiner*—Tai V. Duong
*Attorney, Agent, or Firm*—Renner, Otto, Boisselle & Sklar

[57] ABSTRACT

A welding helmet including an optical protective lens including one or more liquid crystal cells as a variable optical transmission device responsive to a prescribed input to vary light transmission and light blocking characteristics thereof, and a hot mirror band pass filter having a relatively wide transmission characteristic in the visible spectrum and filtering characteristics in the infrared spectrum, the variable optical transmission device being tuned to provide a warning to indicate a nonoperating condition; and the variable optical transmission device being operative in a drive to dark mode for fast operation. Also disclosed is a method for protecting the eyes of a welder while providing a bright clear state, a fast switching to dark state, and the providing of an indication of a power off or failure state.

17 Claims, 2 Drawing Sheets

EYE PROTECTION DEVICE FOR WELDING HELMETS AND THE LIKE WITH HOT MIRROR AND INDIUM TIN OXIDE LAYER

TECHNICAL FIELD

The present invention relates generally, as is indicated, to the control of transmission of electromagnetic energy, especially for controlling transmission of light, and, more particularly, the present invention relates to improvements for automatically controlling light transmitted through a lens in an eye protection device, such as a welding helmet or the like, to provide a relatively dark state and a relatively bright clear state.

BACKGROUND

An example of a lens and welding helmet which has both a rapid driven to dark state during which eye protection is provided during welding, a clear state during which increased clarity is provided for viewing through the lens when welding is not occurring, and a fall state that provides a dark condition for eye protection, for example, if lens power were to fall during welding is disclosed in U.S. Pat. No. 5,208,688.

Such patent discloses a light transmission control device including a band pass filter for transmitting light of a prescribed wavelength or group of wavelengths and for partially blocking transmission of light of a different prescribed wavelength or group of wavelengths, and a variable optical filter for controllably transmitting light of a wavelength or group of wavelengths, for example, as a function of tuning, and wherein the band pass filter and variable optical filter are cooperatively related to provide at least three different light transmitting modes, including relatively maximum transmission, relatively minimum transmission, and a third mode that is less transmissive that the maximum transmissive mode. Due to the filtering by the band pass filter provided in at least part of the visible spectrum range and to the cooperation between the band pass filter and the variable optical filter, intensity or brightness of transmitted light during clear state or maximum transmission state is reduced relative to the intensity of the light incident on the device. It would be desirable to increase the brightness of the clear state of the device.

One type of band pass filters used are those which filter infrared energy to block transmission to the eyes of a welder. A current industry standard requires blocking of electromagnetic energy (or light) in the range of from about 780 nm to about 2000 nm. Although band pass filters have been used in prior welding lenses, for example, to block infrared energy, in prior automatic darkening welding lenses usually one or more band pass filters were used to filter, i.e., to reduce transmission of, at least some light in the visible spectrum. Such visible light filtering provided some optical protection for the eyes of a welder in case of a failure in the variable optical filter of the lens. However, such visible light optical protection by the band pass filter limited the maximum brightness of the lens in the clear or maximum transmissive mode. It would be desirable to increase brightness or transmission in the maximum transmissive mode of such lenses.

It would be desirable to provide an improved variable light transmission controlling device, especially one for use in welding helmets or the like, which provides a clear state that is more transmissive than in prior devices thereby to improve viewing when welding is not occurring, and a dark state for eye protection during welding. It also would be desirable to provide in the device capability to have an intermediate state which in a power off or a failure mode, such as in the absence or inadequacy of power to the device, is darker than the clear state and/or provides a warning to the welder, e.g., that power is off or inadequate or that some other problem exists. It would be further desirable to provide such characteristics while also providing fast operational speed for the light transmission controlling device in switching to the dark state, for example, by providing switching to the dark state as a powered or driven condition of the lens.

Welding helmets have been used in the past to protect the eyes and face of a person doing welding (hereinafter referred to as a welder) from the very bright light occurring during welding, e.g., emanating from the welding arc, and from possible particles that may be flung toward the welder during welding. Early welding helmets had a lens through which a welder would view the work being welded and a protective shield material, such as metal, plastic or other solid material, that contained the lens and protected the welder's face from the light emitted by the welding operation and from particles. Typically the lens was a material that would transmit a relatively small amount of the incident light and, thus, when the welding was occurring would permit enough light to pass to the welder's eyes to observe the welding operation while blocking a substantial amount of the light occurring during welding so that the eyes would not be injured. Sometimes the lens was used in spectacle frames for eye protection without the face protecting shield.

Early welding helmets suffered from the disadvantage that the lenses were of fixed light transmission characteristic, i.e., darkness. Since the lenses were adequately dark (non-transmissive of or able to block transmission of some light) to perform eye protection function, it was difficult or even impossible in the absence of the welding arc to see through the lens to start a welding torch, arc, etc.

Efforts were made to provide variable light transmission characteristics in welding lenses and/or in welding helmets using such lenses. Several examples included variable mechanical devices, such as mechanical shutters located over the viewing area of the welding helmet to control the aperture through which light may be transmitted to the eyes of the welder. Sensors detected the occurrence of the welding light and caused a circuit automatically to close the shutter aperture.

Another early mechanical shutter used relatively rotatable polarizers in optical series. Depending on the brightness or "clearness" desired (or darkness or light attenuation desired) one polarizer was rotated relative to the other. A sensor for detecting incident light and a circuit responsive to the sensor controlled the relative rotation of the polarizers.

An example of a variable solid crystal welding lens with polarizers in protective eye glasses (spectacles) or goggles is disclosed in Marks et al. U.S. Pat. No. 3,245,315.

Other efforts made to provide variable light transmission characteristics for a welding lens have used variable liquid crystal light shutter devices. Two examples of twisted nematic liquid crystal cells used in welding lens assemblies in welding helmets are disclosed in U.S. Pat. Nos. Re. 29,684 (Gordon) and 4,039,254 (Harsch). In the Gordon light shutter a twisted nematic liquid crystal cell, sandwiched between crossed polarizers, rotates the plane of polarized light received from one polarizer to pass it through the second polarizer, thus allowing a welder to see in the absence of a welding arc. In response to welding light being detected by a sensor, a circuit energizes the twisted nematic liquid crystal cell so that polarized light remains unrotated and crossed polarizers block light transmission. In Harsch minimum light transmission occurs in the de-energized (dark) state and maximum transmission occurs when the liquid crystal cells are energized (clear state). In Harsch three polarizers and two twisted nematic liquid crystal cells are arranged such that residual leakage of light through the upstream pair of polarizers and liquid crystal cell when minimum transmission is intended will be reduced by cooperation with the downstream liquid crystal cell and the further polarizer without substantially reducing transmission when in the clear (energized) state.

Alignment of three parallel directionally aligned polarizers and two twisted nematic liquid crystal cells (the five being arranged alternately in tandem to provide selective control of light transmission) also is disclosed in Fergason U.S. Pat. No. 3,918,796.

Before the invention of U.S. Pat. No. 5,208,688 a problem encountered with prior automated welding lenses, especially liquid crystal lenses, is that they have had only two operational states, a dark state and a clear state. If there were a power failure (no or too little power to the lens), the lens would fail to a predetermined state, either clear or dark. Due to characteristics of the twisted nematic liquid crystal cell, if failure were to the dark state, then speed is sacrificed; if failure were to the clear state, then eye protection upon occurrence of a power failure is sacrificed.

In a twisted nematic liquid crystal cell, e.g., as is disclosed in U.S. Pat. Nos. Re. 29,684 and 4,039,254, the twisted nematic liquid crystal is placed between a pair of plane polarizers (also referred to as linear polarizers). Light incident on the first polarizer is linearly polarized thereby and directed through the twisted nematic liquid crystal cell to the second polarizer. In the absence of an electric field input to the twisted nematic liquid crystal cell, the plane of polarization is rotated, for example, ninety degrees as the light is transmitted through the cell. Such light transmission through a twisted nematic liquid crystal cell sometimes is referred to as wave guiding of the light. In the presence of an electric field sufficient to cause alignment of substantially all of the liquid crystal material in the cell with respect to such field, the plane polarized light incident on the cell is transmitted therethrough without such rotation. Depending on the orientation of the second polarizer (also sometimes referred to as the analyzer or analyzer polarizer) relative to the first polarizer, polarized light will be transmitted or blocked, as a function of alignment of the liquid crystal material in the cell and, thus, of whether or not electric field is applied.

A liquid crystal cell may be formed by a pair of generally parallel plates and liquid crystal material sandwiched therebetween, e.g., as in the several liquid crystal cells mentioned in this Background. However, it will be appreciated that a liquid crystal cell used in a welding lens or other device which embodies the principles or features of the invention alternatively may include several such liquid crystal cells in side by side relation to make up a larger area liquid crystal cell. Alternatively, other liquid crystal devices which perform functions similar and/or equivalent to those described for the liquid crystal cells herein also may be employed as a liquid crystal cell according to the invention.

Another type of liquid crystal light control device is known as a dyed liquid crystal cell. Such a dyed cell usually includes nematic liquid crystal material and a pleochroic dye that absorbs or transmits light according to orientation of the dye molecules. As the dye molecules tend to assume an alignment that is relative to the alignment of the liquid crystal structure or directors, a solution of liquid crystal material and dye placed between a pair of plates will absorb or transmit light depending on the alignment of the liquid crystal material. Thus, the absorptive characteristics of the liquid crystal device can be controlled as a function of applied electric field.

A surface mode liquid crystal cell, which is still another type of liquid crystal cell, and devices using such a cell are disclosed in U.S. Pat. Nos. 4,385,806, 4,436,376, Re. 32,521, 4,540,243, and 4,582,396. In contrast to the wave guiding type operation of a twisted nematic liquid crystal cell, the surface mode liquid crystal cell operates on the principle of optical retardation, and, in particular, it operates to retard one of the two quadrature components (sometimes referred to as ordinary ray and extraordinary ray, respectively) of plane polarized light relative to the other. Thus, a surface mode liquid crystal cell effectively can rotate the plane of polarization of plane polarized light by an amount that is a function of a prescribed input, usually an electric field. A surface mode liquid crystal cell in effect is a variable optical retarder or variable wave plate that provides retardation as a function of the prescribed input.

Briefly, a surface mode liquid crystal cell is constructed of nematic liquid crystal (or liquid crystal that functions like nematic liquid crystal insofar as indices of refraction, birefringence, structural alignment, etc. characteristics are concerned) and a pair of generally parallel plates, each having been rubbed or otherwise treated at one surface thereof to effect desired alignment of the liquid crystal structure at the surfaces. The rub directions, for example, of the surfaces of the two plates forming the surface mode liquid crystal cell are parallel, i.e., generally in the same or opposite direction, to each other rather than at a right angle to each other (the case of the twisted nematic liquid crystal cell). Treatment also may provide for a tilt angle of the liquid crystal directors at the surfaces, as may be desired for various operational results, as is well known in the art.

The surface mode liquid crystal device may be wavelength sensitive in that the amount of retardation for a given set of conditions thereof is a function of the wavelength of the incident light. Depending on the birefringence of the liquid crystal material in a surface mode liquid crystal cell, the thickness of the layer of liquid crystal material in the cell, the magnitude of the applied prescribed input, usually electric field, when applied and the technique with which the surface mode liquid crystal cell is driven, the amount of retardation can be controlled or determined. These considerations and features are described in the above-mentioned U.S. patents related to surface mode liquid crystal cells and devices and in other literature.

In a surface mode liquid crystal cell that is positioned between a pair of plane polarizers, the amount of retardation of plane polarized light incident on the cell can be determined as a function of the aforementioned characteristics, including, as well, the wavelength of the incident light. In fact, depending on the wavelength makeup of the incident light, the effective thickness of the birefringent liquid crystal layer(s) in the cell, and the birefringence of that (those) layer(s), optical color dispersion may occur. (The principles of optical color dispersion, birefringence, optical polarization and polarized light are described in *Fundamentals of Optics* by Jenkins and White, McGraw-Hill Book Company, New York, 1976.) Moreover, depending on the plane of polarization of the output light transmitted through the cell and output therefrom and the relative directional orientation of the output plane polarizer (analyzer), the intensity of the transmitted light through the output plane polarizer may be varied. Therefor, if the surface mode cell is so constructed and so energized or operated that significant color dispersion does occur, then a color or wavelength filtering function can occur.

Further, a surface mode cell may be so constructed and so energized or operated that significant color dispersion does not occur. This type of operation occurs when the surface mode liquid crystal cell is operated at or near what is referred to as zero order. In such operation intensity modulation of the light output from the cell can be achieved with substantial uniformity (so that there is no or only minimal distortion of the transmitted images) and without color dispersion so that the lens essentially is achromatic.

As will be described further below, the present invention is directed to a variable optical transmission controlling device which has at least three different output conditions. The device is described in detail with respect to use in a welding helmet. However, it will be appreciated that the device may be employed in other environments and in other devices and systems for controlling transmission of electromagnetic energy broadly, and, in particular, optical transmission. As used herein with respect to the preferred embodiment, optical transmission means transmission of light, i.e., electromagnetic energy that is in the visible spectrum and which also may include ultraviolet and infrared ranges. The features, concepts, and principles of the invention also may be used in connection with electromagnetic energy in other spectral ranges.

The invention is especially useful for eye protection wherein high speed protective shuttering and protective fail state are desired. Exemplary uses are in welding helmets, spectacles, goggles, and the like, as well as safety goggles for nuclear flash protection, for protection from hazards experienced by electric utility workers and for workers at furnace and electrical plant areas and at other places where bright light that could present a risk of injury may occur.

Further, the invention is described herein as undergoing certain operation in response to a prescribed input. The preferred prescribed input is an electric field. However, it will be appreciated that other prescribed inputs may be used, and reference to electric field may include equivalently such other prescribed inputs. For example, as is known, liquid crystal cells are responsive to magnetic field inputs and to thermal inputs. Other inputs also may be possible to obtain generally equivalent operation.

As is well known, the transition speed for a liquid crystal cell, whether of the twisted nematic type, dyed cell type or surface mode type, is asymmetrical; in particular, such a liquid crystal cell operates faster to achieve an operational condition, e.g., alignment of liquid crystal structure or directors, when driven to that condition by an electric field (or an increase in the field magnitude), than it operates when relaxing to a de-energized or reduced energization state, e.g., reduction or elimination of the electric field. Therefore, for maximum speed of operation to the dark state for eye protection, for example, it is desirable in a welding lens environment that the liquid crystal lens be operated with maximum power to achieve the darkest eye protection state. Also, a surface mode liquid crystal cell usually responds to energization significantly faster than a twisted nematic liquid crystal cell, and it, therefore, provides for faster operation in accordance with the present invention.

Shade number or shade is the characterization of darkness of a welding lens, for example, (hereinafter sometimes simply referred to as lens); a larger shade number represents a darker, more light blocking (or absorbing) or less optically transmissive lens and a smaller shade number represents a less dark, less light blocking (or absorbing) or more optically transmissive lens. Generally optical transmission means transmission of light and the image or view carded by the light without substantial distortion of those images, e.g., due to scattering. Shade number is a term of art often used in the field of welding and especially welding lenses for eye protection.

Clear state or clear shade means the state of highest operating luminous transmittance (or light transmission) of the lens. This state corresponds to the state having the lowest shade number for the lens.

Dark state or dark shade is the lowest operating luminous transmittance (or light transmission) of the lens. This state corresponds to the state having the highest specified shade number for the lens. The invention is described below in some instances indicating that in the dark state no light is transmitted. While this may be desirable for some applications of the principles of the invention, it will be appreciated that for a welding lens in the dark state there will be some transmission so that the welder can see to do the welding while some light is blocked to provide the desired eye protection from damage, injury or the like by the light emitted during welding.

Intermediate state or intermediate shade is one that is not the clear state and the dark state. It may be between the clear state and the dark state, but this is not always necessary, for it may even be darker than the dark state if such operation could be achieved. According to the described embodiment of the invention, the intermediate state provides a level of light transmission/absorption different from the clear state and occurs during power failure, inadequate power, or power off status of the lens.

Power failure, failure, or fail state means absence of power being delivered to the lens. Power failure also may mean that inadequate power is being delivered to the lens to cause it to assume the desired state.

Off state is the condition of the lens when no electrical power is being supplied to the lens; the off state also is referred to as the power-off state. As is described below, the intermediate shade preferably occurs in the welding lens during the off state. The fail state of the lens also may be the off state, i.e., no power is provided due to failure of the power supply or simply the power has not been turned on or has been turned off; and the fail state also may occur when there simply is inadequate power available to drive or to energize the lens to the clear state and dark state.

Shutter response time is the time required for the circuitry associated with the lens to detect a sharp increase in incident light (e.g., due to striking of the welding arc, etc.) and to switch the lens from the clear state to the dark state.

Shutter recovery time is the time required for the circuitry associated with the lens to detect a sharp decrease in light (e.g., due to extinguishing of the welding arc, etc.) and to switch the lens from the dark state to the clear state.

Variable transmittance is the ability of the lens to be switched from one level of luminous transmittance (also referred to as transmission of light) to another level of luminous transmittance in response to a change in incident illumination.

Dynamic operational range or dynamic optical range is the operational range of the lens between the dark state and the clear state, e.g., the difference between the shade numbers of the dark state and the clear state.

As was mentioned above, a problem encountered with prior automated welding lenses, especially liquid crystal lenses, is that they have only two operational states, a dark state and a clear state. If there were a power failure (no or too little power to the lens), the lens would fail to a predetermined state, either clear or dark. If failure were to the dark state, then speed is sacrificed; if failure were to the clear state, then protection upon occurrence of a power failure is sacrificed.

The entire disclosures of all of the above-mentioned patents and patent applications are hereby incorporated by reference.

As used herein, the term wavelength may mean either a specific wavelength of electromagnetic energy, such as light having a wavelength 550 nm, or a group of wavelengths, such as light falling within the group of wavelengths 550 nm to 600 nm, etc. Also, reference to one wavelength being different from another may mean that the specific wavelengths are different, e.g., as 550 nm wavelength light is different from 600 nm wavelength light; it also may mean that the collection of wavelengths of one group of wavelengths differs from that of another group of wavelengths; and it also may mean that if two groups of wavelengths have the same collection of wavelengths, the intensity or magnitude of a given wavelength of one group differs from the intensity or magnitude of that wavelength of the another group.

SUMMARY

Briefly, the invention relates to use in a welding lens of a band pass filter that has a relatively bright or clear transmission characteristic in the visible spectrum and filters out infrared. Such a band pass filter does not significantly cooperate with the variable shutter of the welding lens to limit transmission in the intermediate, off a failed condition.

An aspect of the invention is to use a variable optical filter to control light transmission in an optical device, such as a welding lens, goggles, helmet or the like or in some other device, and to provide further light filtering by a band pass filter which provides relatively high transmission in a relatively broad spectrum in which the variable optical filter also selectively can transmit light and relatively minimal transmission in a different part of the energy spectrum, such as infrared.

According to an aspect of the invention, a light transmission control device includes a band pass filter for transmitting light of a group of wavelengths and for substantially blocking transmission of light of a different group of wavelengths, and a variable optical filter for controllably transmitting or blocking light of a wavelength or group of wavelengths and that also can control transmission as a function of tuning, and wherein the variable optical filter provides at least three different light transmitting modes, including relatively maximum transmission, relatively minimum transmission, and a third mode that is less transmissive than the maximum transmissive mode.

According to an aspect of the invention, a light transmission control device includes a band pass filter for transmitting light of a group of wavelengths and for substantially blocking transmission of light of a different group of wavelengths, and a variable optical filter for controllably transmitting light and wherein the variable optical filter provides at least three different light transmitting modes, including relatively maximum transmission, relatively minimum transmission, and a third mode, and wherein conditions exhibited by the third mode provide an indication that the device is not off, is properly operational to furnish the desired minimum transmission mode or the like.

According to an aspect of the invention, a light transmission control device includes a band pass filter for transmitting light of a group of wavelengths and for substantially blocking transmission of light of a different group of wavelengths, and a variable optical filter for controllably transmitting light of a wavelength or group of wavelengths, and wherein the variable optical filter provides at least three different light transmitting modes, including relatively maximum transmission, relatively minimum transmission, and a third mode, and wherein the variable optical filter is tuned by construction thereof for the third mode so that in the absence of power, in the case of insufficient power, or the like, the variable optical filter substantially blocks some light as a function of wavelength and transmits at least some light at a different wavelength to indicate the condition of the device.

According to an aspect of the invention, a light transmission control device includes a band pass filter for transmitting light of a group of wavelengths and for substantially blocking transmission of light of a different group of wavelengths, and a variable optical filter for controllably transmitting light of a wavelength or group of wavelengths, and wherein the variable optical filter provides at least three different light transmitting modes, including relatively maximum transmission, relatively minimum transmission, and a third mode that is less transmissive than the maximum transmissive mode, and wherein the relatively maximum transmission mode is substantially neutral color or filtering.

An aspect of the invention relates to controlling transmission of light energy which has a plurality of wavelengths incident thereon, by filtering light using a band pass filter for transmitting a substantial amount of such light energy in the visible range and for filtering at least some of such light energy of at least one other wavelength, e.g., infrared and variably filtering such light by an electronically controlled variable optical filter.

Yet another aspect of the invention is to provide the various features disclosed and claimed herein in an eye protection device, and especially in a welding lens, helmet, goggles, spectacles or the like, for protecting the eyes of a welder, or the like.

In the description below, an embodiment of the invention which uses surface mode liquid crystal cell technology for the variable optical filter is presented. It will be understood, though, that other types of variable optical filters additionally or alternatively may be used in accordance with the invention. Examples of other types of variably optical filters include twisted nematic liquid crystal, supertwist twisted nematic liquid crystal, ferroelectric liquid crystal, PLZT and/or other technology and devices.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed.

Although the invention is shown and described with respect to certain preferred embodiments, it is obvious that equivalents and modifications will occur to others skilled in the art upon the reading and understanding of the specification. The present invention includes all such equivalents and modifications, and is limited only by the scope of the claims.

DETAILED DESCRIPTION

Figures 1, 2, 3, 4, 5:
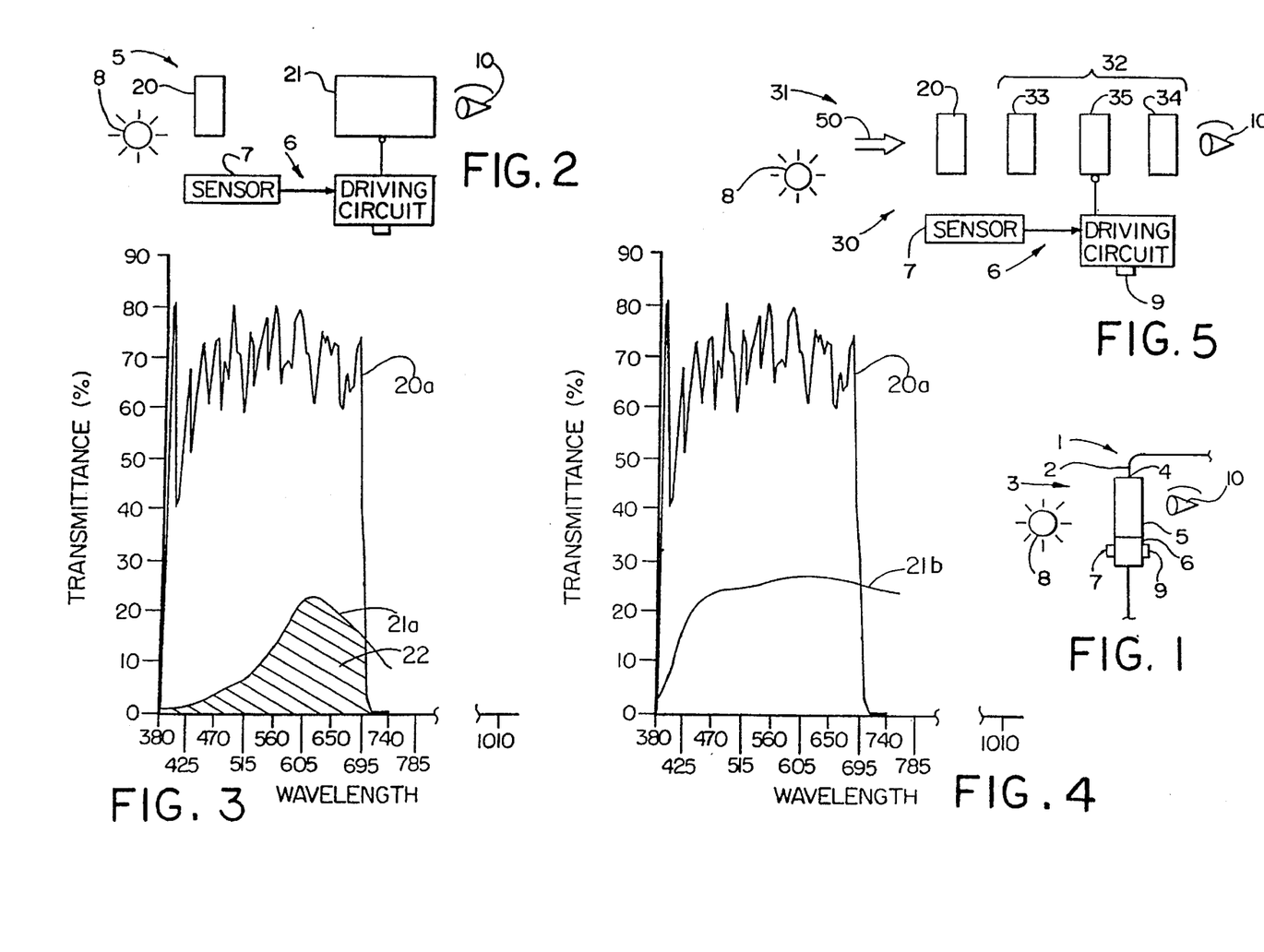
FIG. 1 is a schematic view of a welding helmet with a variable liquid crystal lens in accordance with the present invention.
FIG. 2 is a schematic view of the lens of FIG. 1.
FIG. 3 is a graph depicting the optical transmission characteristics of the band pass filter and the controllable variable wavelength transmission controlling device used in the lens of FIG. 2 to show the intermediate transmission state thereof.
FIG. 4 is a graph depicting the optical transmission characteristics of the band pass filter and the controllable variable wavelength transmission controlling device used in the lens of FIG. 2 to show the clear transmission state thereof.
FIG. 5 is a schematic view of an embodiment of the lens of FIG. 2 using a pair of plane polarizers and a surface mode liquid crystal cell therebetween, directions of polarization and/or of axes of various optical elements are indicated by arrows pointing up indicating relatively vertical or angularly indicating at an angle relative to vertical and/or to horizontal, and/or by "X" indications representing direction into the plane of the paper, the same convention being employed in the other drawing figures.

Referring, now, in detail to the drawings, wherein like reference numerals designate like parts in the several figures, and initially to FIG. 1, a welding helmet 1 according to the invention includes a protective shield 2 and a filter assembly 3 mounted in the shield. The shield 2 may be of generally optically non-transmissive material, such as metal, plastic, or other material to protect a welder's face and/or head as is conventional. The filter assembly 3 may be permanently mounted in an opening 4 of the shield 2, or means (not shown) may be provided to hold the filter assembly 3 in the opening 4 and also to permit removal of the filter assembly from the shield, if desired.

The filter assembly 3 itself includes a welding lens 5 and a driving circuit 6 for supplying a prescribed input to the welding lens 5 to effect operation. Preferably that input is an electric field produced by a voltage from the driving circuit 6 suitable to operate a liquid crystal cell in the welding lens, as is described further below. However, it will be appreciated that the prescribed input may be other than an electric field, for example, a magnetic field, thermal energy, or some other prescribed input that will operate the welding lens 5.

The welding lens 5 is of a type that can achieve three different optical states, namely a clear state, a dark state, and a third state (referred to below as an intermediate state) of optical transmission that is different from the clear state and the dark state. The intermediate state has a transmissive quality that preferably is darker than the clear state, and likely, but not necessarily, less dark than the dark states i.e., between the clear state and the dark state (as is described below in the illustrative examples of the invention). Preferably the intermediate state is of a character, e.g., a color, that indicates to a welder that the welding lens 5 is off or is not operative to provide the expected protection of the dark state. Moreover, the welding lens 5 preferably is of the type that assumes the intermediate state in the absence of power being supplied thereto by the driving circuit 6 or when the power level supplied is inadequate; assumes the clear state in the presence of a first electric field input, i.e., an electric field of a first magnitude; and assumes the dark state in the presence of a second electric field input, i.e., an electric field which is of greater magnitude than the first.

Although the preferred embodiment employs the lens 5 in a welding helmet 1, the lens may be used for other eye protection functions or other functions in accordance with the operative principles described herein. As will be appreciated, the lens provides control of the intensity of light transmitted therethrough, for example, to the eyes of a welder. Preferably such transmission is without degradation of the image characteristics of the transmitted light, thus, enabling an object, scene, etc. to be viewed without distortion. Moreover, it will be appreciated that although the lens of the invention preferably is used to protect the eyes of a person, it may be used to control transmission of electromagnetic energy for other purposes as well.

The driving circuit 6 includes a source of electric power, e.g., a storage battery, photovoltaic cell, transformer connection to some other power source (such as that available through an electrical receptacle), etc., and circuitry necessary to establish the requisite electrical field across the liquid crystal cell in the welding lens 5. A sensor or detector 7, which may be part of the driving circuit, is cooperative with the driving circuit to detect the intensity of incident light and to produce an electrical field having a voltage which is analog or step-wise proportional in amplitude to the intensity of such incident light. More particularly, when the intensity of light incident on the sensor 7 is less than that occurring during welding, the driving circuit 6 produces an electric field which energizes or drives the welding lens 5 to the clear state; and when light incident on the sensor 7 is representative of the occurrence of welding (e.g., commencing immediately upon striking of the welding arc represented at 8), the driving circuit 6 produces an electric field which energizes or drives the welding lens 5 to the dark state. Exemplary driving circuits are described in copending U.S. patent applications Ser. No. 07/674,850, filed Mar. 25, 1991 (now U.S. Pat. No. 5,252,817, issued Oct. 12, 1993), 07/814,372, filed Dec. 26, 1991 (now U.S. Pat. No. 5,248,880, issued Sep. 28, 1993), 07/943,994, filed Sep. 10, 1992 (now U.S. Pat. No. 5,347,383, issued Sep. 13, 1994), 08/027,235, filed Feb. 17, 1993, and 08/013,966, filed Feb. 5, 1993 (now U.S. Pat. No. 5,377,032, issued Dec. 27, 1994), the entire disclosures of which are incorporated by this reference. Other driving circuits also may be used and/or designed that perform the various functions energizing the liquid crystal lens in the described manner. Should the driving circuit fail such that power is not provided the welding lens in particular (or that provided is inadequate), the welding lens will assume the intermediate state or shade, as is described in further detail herein.

Using the welding helmet 1, a welder would press a power switch 9 to turn on the driving circuit 6 to energize the welding lens 5 to the clear state; and then the welder would place the helmet on his or her head generally aligning the welding lens 5 with the eyes 10. As a result of energizing the welding lens 5 to the clear state, the welder then can see through the welding lens to place the welding tools in proximity to a work piece intended to be welded. Upon the inception of welding, e.g, striking of the welding arc, the sensor 7 detects the same and causes the driving circuit 6 to energize the welding lens 5 to the dark state. The dark state is designed to protect the eyes of the welder from damage due to the electromagnetic emissions, in particular the intense light emitted during welding. In case the driving circuit 6 were to fail during use or did not energize the welding lens when the power switch 9 is closed, the welding lens 5 would preferably promptly assume the intermediate state, which indicates caution or a warning to the welder that the welding lens is off or is not able to operate to provide the dark state and also may be sufficient to provide a measure of protection to the eyes of the welder until the welding action if already occurring is terminated.

The shield 2 and the filter assembly 3 preferably are adequately strong to protect the face of the welder from particulates possibly emitted during welding; and the shield itself also preferably is not optically transmissive so that it provides protection from electromagnetic energy for the face and eyes of the welder during welding.

Turning to FIG. 2, the features of the welding lens 5 are shown. The welding lens 5 includes a band pass filter 20 and a controllable variable wavelength light transmission controlling device 21 which are in optical series so that light from welding operation, e.g., emitted by a source 8, such as the welding arc, will have to pass through both before reaching the eyes 10 of the welder. Optically, it does not matter which of the filter 20 or device 21 is closer to the welding arc source 8 and which is closer to the eyes 10. However, in the preferred embodiment the band pass filter 20 is placed optically upstream (relative to the eyes 10) of the variable device 21. Since the filter 20 preferably is not dynamic or actively changed, and, therefore, is less subject to damage than the device 21, since it preferably has a hard exterior surface, such as glass or quartz, etc., for strength and durability, and since it preferably blocks transmission of infrared wavelengths of electromagnetic energy which may be damaging to at least some liquid crystal cells and/or materials thereof, this positioning will avoid subjecting the optically active device 21 to unnecessary damage and may increase longevity.

The band pass filter 20 may be a conventional optical band pass filter which transmits light in a prescribed wavelength region and blocks transmission of light (filters out light) in a different wavelength region or regions. For example, referring to the primary colors (red, green and blue), the band pass filter may transmit blue light and partially block (filter) red light and green light. Preferably the band pass filter 20 transmits substantially all light in the visible spectrum, e.g., from about 380 nm to about 700 nm and substantially blocks transmission of infrared light. It also may block ultraviolet light. Exemplary band pass filters are sold by Optical Coating Laboratory, Inc., of Santa Rosa, Calif. as Coolbeam™ wide band hot mirrors. Such hot mirrors preferably have an additional coating of indium tin oxide to provide adequate filtering of infrared energy to 2000 nm.

An example of the transmission characteristics of such a band pass filter 20 is represented by curve 20a in FIG. 3. In FIG. 3 the vertical axis represents as a percentage the ratio of light incident on the particular device to that transmitted through the device, such as the band pass filter 20 or the variable device 21, and the horizontal axis represents the wavelength of such light. In FIG. 3 the horizontal axis stops at about 1050 nm; preferably curve 20a remains at about zero percent transmittance to 2000 nm. Curve 20a depicts a maximum transmission of from about 40% to about 80% for light incident on the band pass filter 20 having a wavelength in the visible spectrum or from abut 380 nm to about 685 nm. Curve 20a also depicts how the amount of light that is transmitted by the band pass filter 20 decreases to about zero percent of the incident light as the wavelength of the incident light approaches and exceeds about 695 nm.

The controllable variable wavelength transmission controlling device 21 is a device that has the ability to control transmission and blocking of light, and under prescribed circumstances to effect such control as a function of the wavelength of the light incident thereon. More particularly, the device 21 is tuned so that in the absence of a power input (hereinafter referred to as the power off or fail mode or state), or under some other circumstance which preferably is predetermined, it will block transmission of some light so as to present a cautionary warning to indicate either that the power is off; or that the filter assembly is inoperable, is without power, or in any event is not able to provide the desired protection; or both. Furthermore, the device 21 is operable to a clear state having a maximum transmission of light incident thereon substantially independent of wavelength and to a dark state blocking substantially all of the light incident thereon, thus also being substantially independent of wavelength.

Since the hot mirror band pass filter 20 transmits light substantially uniformly in the visible spectrum, and since the variable device 21 in the clear state transmits light substantially independent of wavelength, too, in the clear state the lens 5 is a neutral filter for visible light. This characteristic of the lens 5 improves viewing in the clear state generally maximizing the completeness and clarity of transmitted images especially without blocking some visible wavelengths.

In FIG. 3 curve 21a represents the tuned condition of the device 21 in the power off mode. It can be seen that there is maximum transmission of about 20% of the incident light when that incident light has a wavelength of about 600 nm, and the transmission decreases on either side of that maximum. There is a portion 22 in the graph of FIG. 3 where curves 20a and 21a overlap and encompass a commonly included area (shown by hatching in the figure) representing transmission by both the band pass filter 20 and the variable device 21. That portion 22 indicates that in the power off mode, some light will be transmitted through the welding lens 5. Since the band pass filter 20 only outputs or transmits through it some of the total incident light energy directed to the welding lens 5 according to the curve 20a of FIG. 3, and since the controllable variable device 21 only transmits a part of the light it receives from the band pass filter 20, e.g., according to the curve 21a, then, in the illustrated example in FIG. 3, the amount of light transmitted or output by the welding lens 5 in the power off mode is the product of the percent transmission by the band pass filter 20 and the percent transmission by the controllable variable device 21. Thus, if the band pass filter transmits about 70% of the incident light at 550 nm and at 550 nm the controllable variable device 21 transmits about 17% of the light received from the 550 nm, then the light output by the welding lens 5 at 550 nm would be I*70%*17%, where I is the intensity of incident light on the welding lens 5; and such light output by the welding lens, of course, would be different for different wavelengths.

Desirably the characteristics of the controllable variable wavelength transmission controlling device 21 are selected such that in case there is an accidental power off or power failure occurrence of the driving circuit 6, the welder will be warned and relatively promptly will terminate the welding operation. The warning is in the color of the light transmitted by the welding lens 5, which preferably is largely red due to the tuning of the variable device 21 for zero power operation. Since the hot mirror 20 transmits most visible light uniformly it is in a sense a neutral filter. The variable filter 21 transmits red light when unpowered and mostly blocks other colors of the visible spectrum. Therefore, when the variable device 21 is off or not operating, the light transmitted through the welding lens will be colored red or tinged red.

Briefly referring to the graph of FIG. 4, which has the same vertical and horizontal axes representing percent optical transmission and wavelength of incident light respectively, the optical transmission curve 21b for the device 21 during energization by the driving circuit 6 to the clear state is shown relative to the same curve 20a described above with respect to FIG. 3. Such clear state preferably encompasses all area encompassed by the curve 20a, which represents the optical transmission characteristics of the band pass filter 20. Therefore, in the clear state the welding lens 5 will preferably transmit the maximum amount of light of which the optical series arrangement of the individual components thereof are capable. In the preferred embodiment the device 2 1 in the clear state is as transparent as possible to visible light substantially independent of wavelength (or at least is sufficiently transparent as to transmit substantially all light received from the filter 20), and such characteristic is evident from the curve 21b. It will be appreciated that in the example presented in FIG. 4, the controllable variable device 21 tends to transmit approximately 25% of the light incident thereon regardless of wavelength (at least in the operating wavelength range of the welding lens 5 as determined by the band pass filter 20 and curve 20a); therefore, the amount of light transmitted by the welding lens 5 in the clear state represented by the graph of FIG. 4 would be about 25% of the light that is received by the device 21 from the band pass filter 20.

No graph is shown for operation of the welding lens 5 in the dark state. In such dark state the band pass filter 20 maintains its optical transmission characteristics which are represented in curve 20a; however, the controllable variable wavelength transmission controlling device 21 is energized to block substantially all light incident thereon substantially independent of wavelength. Therefore, there will be substantially no light transmission by the welding lens 5 during such energization other than a small amount due to the substantial brightness of the welding operation, which enables the welder to see such operation without injury to the eyes. Moreover, such dark state is produced, as will be described in further detail below, in response to the application of a relatively maximum electric field to the device 21 compared to a lesser field being applied during the clear state and zero field state during the power off mode. Accordingly, switching to the dark state will be relatively fast.

An embodiment of filter assembly 30 for use in the welding helmet 1 is illustrated in FIG. 5. The filter assembly 30 includes the driving circuit 6 and a welding lens 31. The welding lens includes the band pass filter 20 and a controllable variable wavelength transmission controlling device 32, which are cooperatively interrelated to function generally in the manner described above with respect to the filter assembly 3 shown in FIGS. 1 and 2. The device 32 includes a pair of plane polarizers 33, 34 and a surface mode liquid crystal cell 35. The optically upstream polarizer 33, i.e., the one closer to the source of light 8, will be referred to as the polarizer for the device 32, and the polarizer 34, which is at the optically downstream side of the cell 35, sometimes will be referred to as the analyzer, as is conventional. The cell 35 is coupled to the driving circuit 6 for controlled energization thereof as a function of intensity of light incident on the sensor 7. Overall construction and operation of the surface mode liquid crystal cell 35 are described in several of the above-mentioned incorporated patents and are known in the art at this time. As is described in such patents, preferably the axis of the surface mode liquid crystal cell (i.e., the rub direction described further below) is oriented approximately at about 45 degrees relative to the polarization direction of the polarizers 33, 34. This will maximize and optimize utilizing the birefringence characteristics of the surface mode liquid crystal cell.

The lens 31 operates generally in the manner described above for the lens 5; note the discussion regarding operation with respect to the curves and light transmission described with respect to FIGS. 2, 3 and 4. The particularly unique features of the surface mode liquid crystal cell 35 in cooperation with the polarizer and analyzer 33, 34 provide for wavelength dependency during the power off state and for wavelength independent light transmission and darkness during the clear and dark states, as will be described below with respect to FIGS. 6A, 6B and 6C.

The surface mode liquid crystal cell 35 includes a pair of plates 40, 41, usually of glass, plastic or other polymer material, etc., preferably generally transparent to visible light, and positioned generally in parallel planar relationship. The plates 40, 41 define a volume 42 therebetween, which usually is sealed at the edges of the plates, containing liquid crystal material 43. The liquid crystal material 43 preferably is nematic liquid crystal material or operationally nematic liquid crystal material which has the desired optical, alignment, and operational characteristics of nematic liquid crystal. The nematic liquid crystal material has directors or structural alignment characteristics which are influenced by the surfaces 44, 45 of the plates. Those surfaces 44, 45 preferably are pre-treated, e.g., by rubbing in parallel direction or by some other means, to cause alignment of the liquid crystal directors with such rub direction, as is known. Moreover, the plates 40, 41, are positioned so that the rub directions thereof are in the same direction or in an opposite direction (sometimes respectively referred to as parallel and anti-parallel). In the absence of an electric field, the liquid crystal structure will tend to align generally in parallel with such rub directions, as is depicted schematically in FIG. 6A.

Figure 6A:
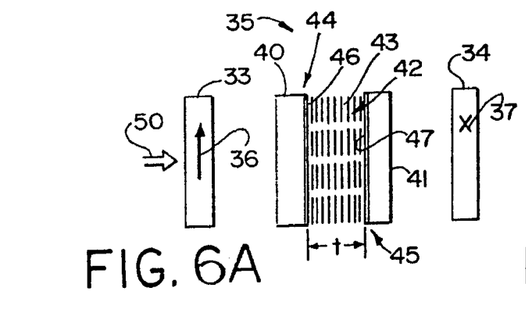
FIG. 6A is a schematic view of a controllable variable wavelength transmission controlling device including a surface mode liquid crystal cell shown in the power off intermediate darkness state for use in the lens of the present invention.

The cell 35 also has electrodes 46, 47 on the surfaces 44, 45 to apply electric field across the liquid crystal material in the cell, as is conventional. Such electrodes may be indium tin oxide (ITO) or some other suitable electrically conductive optically transparent material. Desirably the cell 35 should be protected from the occurrence of short circuits when relatively high voltage is applied. For this purpose several known techniques may be used. One is to provide insulation between the electrodes and the liquid crystal material; an exemplary insulating material is silicon dioxide. Another technique is to provide relatively large contact areas between the respective electrodes and the electrical distribution system that supplies voltage thereto so that the voltage and, thus, the electric field, is supplied as uniformly as possible over the entire electrodes. Other techniques to avoid short circuits in response to relatively high voltage energization also may be used.

Figure 6B:
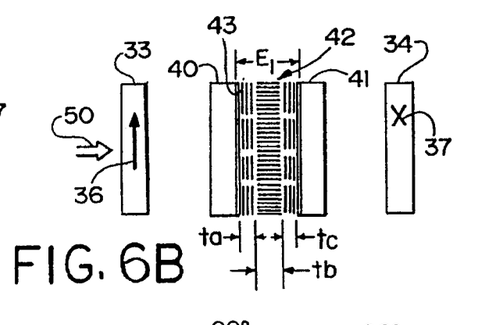
FIG. 6B is a schematic view of the controllable variable wavelength transmission controlling device including a surface mode liquid crystal cell of FIG. 6A, but here shown in the clear state for use in the lens of the present invention.
Figure 6C:
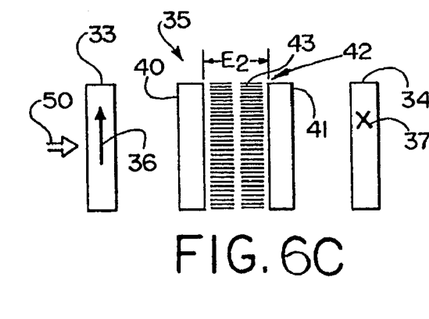
FIG. 6C is a schematic view of the controllable variable wavelength transmission controlling device including a surface mode liquid crystal cell of FIGS. 6A and 6B, but here shown in the dark state for use in the lens of the present invention.

As is seen in FIGS. 6A, 6B and 6C, the plane polarizer 33 and analyzer 34 are crossed, i.e., aligned with the respective axes of polarization or directions of planes of polarization thereof generally at right angle relationship to each other. Therefore, absent the surface mode liquid crystal cell 35, incident light 50 transmitted through the polarizer 33 would be polarized in the plane of polarizer 33, say vertically, as illustrated by the arrow 36, and it would be blocked from transmission through the relatively crossed analyzer 34 which would then be polarized into the plane of the paper, or horizontally, as illustrated by the cross 37.

Intermediate State, Power Off State, Fail State:

In the absence of an electric field, or in the absence of a sufficient electric field, such that the liquid crystal material 43 will be aligned in the manner shown schematically in FIG. 6A, polarized light transmitted through the cell will undergo both optical retardation and color dispersion. Retardation is a function of the equation $$\frac{(\Delta n)*t}{(\lambda)},\qquad\text{(Equation 1)}$$

where ($\Delta n$) is the birefringence or difference between the ordinary and extraordinary indices of refraction of the liquid crystal material; t is the thickness of the layer of liquid crystal material which exhibits the birefringence characteristic, and ($\lambda$) is the wavelength of the light. Since, as is seen from Equation 1, retardation is a function of wavelength, different wavelengths will experience different amounts of retardation during transmission through the cell 35. The retardation function is analogous to that provided by a wave plate. As plane polarized light incident on the cell 35 is transmitted through the liquid crystal material 43, such light will be converted to elliptically polarized light, the direction of the major axis of the ellipse with the extent of ellipticity (i.e., from plane polarized light to circular polarization or ratio of the minor axis to the major axis of the ellipse) being a function of birefringence of the liquid crystal material, thickness of the liquid crystal layer, and wavelength of the light. Thus, the components or magnitudes of the various wavelengths of light that are in the direction of the polarization direction of the analyzer 34 will be different. Therefore, the transmittance of light by the device 32 will vary as a function of wavelength.

The surface mode liquid crystal cell 35 can be tuned to provide the desired warning of inoperability, failure, or power off, by selecting a liquid crystal material with a particular birefringence characteristic and by selecting the particular thickness of the liquid crystal layer 43 so that the wavelength of light that tends to have the greatest transmittance by the device 32 in the absence of an electric field will be of the specified color, e.g., red. Tuning of the surface mode liquid crystal cell may be achieved by selection of the materials thereof (e.g., according to birefringence characteristics of the liquid crystal material which are, of course, well known), by mechanical structure (e.g., according to the spacing of the surfaces between which the liquid crystal material is contained, e.g., on the order of from several to several tens of microns and especially from about 4–20 microns, especially 5–11 microns, and/or according to tilt angle of the liquid crystal at and near the surfaces of the liquid crystal cell), and by electrical input (e.g., the electric field which causes an aligning of liquid crystal structure (directors) with respect to the field and in proportion to the magnitude thereof).

Clear State:

In FIG. 6B the surface mode liquid crystal cell in the controllable variable wavelength transmission controlling device 32 of the lens 31 (FIG. 5) is shown in the clear state. Accordingly, an electric field $E_1$ of a magnitude suitable to align some of the liquid crystal 43 is applied by the driving circuit 6 via the electrodes 46, 47 across the liquid crystal material 43. The liquid crystal preferably has positive dielectric anisotropy so it will align with the electric field as is illustrated to obtain the described optical result. That liquid crystal near the center portion of the cell between the plates 40, 41 aligns with the field, and that liquid crystal nearer the surfaces 44, 45 of the plates remains generally aligned with the surfaces. Such alignment is shown schematically in FIG. 6B. The thicknesses of the several differently aligned portions of liquid crystal are designated $t_a$, $t_b$, and $t_c$. It will be appreciated that although distinctly aligned portions of liquid crystal material are shown, e.g., parallel or perpendicular to the surfaces 44, 45, it is expected that some liquid crystal will be somewhat otherwise angularly oriented at various boundaries, e.g., at the surfaces 40, 41 and/or at the areas where the differently aligned portions come together to provide, for example, a more or less continuous or smooth transition between those portions.

As is known, the liquid crystal material that is in the center of the cell (having a thickness $t_b$) will not have any significant optical affect on light transmitted therethrough due to alignment of the ordinary axis of the liquid crystal material parallel with respect to the direction of transmission of light 50 through the cell. However, that liquid crystal in the surface layers (having thicknesses $t_a$ and $t_c$) is oriented perpendicular to the direction of transmission of light through the cell and, consequently, the cell will exhibit birefringence. Accordingly, light transmission therethrough will vary as a function of the polarization direction of the light, with the effective thickness t of the liquid crystal material exhibiting such birefringence (for use in the above Equation 1) being the sum of the thicknesses of the layers oriented perpendicular to the direction of light transmission, namely the sum of the thickness $t_a$ and $t_c$.

The birefringence of the liquid crystal material 43 and the magnitude of the electric field $E_1$ are selected such that the result of Equation 1 corresponds to substantially a 90° rotation of the plane of polarization for all wavelengths of incident light. ($E_1$ influences Equation 1 indirectly by determining the effective thickness of the birefringent portion of the liquid crystal material, i.e., the thickness $t_a$ and $t_c$.) As can be seen from Equation 1, the smaller the numerator ($\Delta n*(t_a+t_c)$), the smaller the difference in retardation for various wavelengths of light ($\lambda$). Consequently, the numerator of Equation 1 is minimized, while still providing for a degree of retardation corresponding to substantially 90° rotation of the plane of polarization of incident light, to minimize color dispersion. A surface mode liquid crystal device operating in such a manner is said to be operating at zero order. A device operating at a higher order may still provide for the effective 90° rotation of light for one wave length (such as by rotating it 270°, 450°, etc.) but would have a greater difference in the actual retardations for various wavelengths, thus creating color dispersion. Such a high order operating device may be obtained by increasing the thickness of the portion of liquid crystal material oriented perpendicular to the propagation direction of light through the device.

With the retardation occurring in response to application of the field of magnitude $E_1$, the surface mode liquid crystal cell 35 is intended to effect retardation that results in rotation by about 90 degrees of the plane of polarization of the incident plane polarized light received from the polarizer 33. Therefore, the light directed from the cell 35 to the analyzer 34 will be transmitted substantially completely by such analyzer.

The just described operation of the surface mode liquid crystal cell 35 is that of the clear state for the lens 31. Since operation in the clear state is at or approximately at zero order at which there is substantially no color dispersion, light transmission through the controllable variable wavelength transmission controlling device 32 will be independent of wavelength.

Moreover, an advantage of using a surface mode liquid crystal cell and driving it to the clear state as well as in the dark state is the substantial uniformity of optical response across the entire liquid crystal cell due to substantial uniformity of thickness of the birefringent layer(s) t, $t_a$, and $t_b$ when the liquid crystal cell is energized; and this provides for uniformity of the viewed image minimizing the possibility of distortion.

Dark State:

Briefly referring to FIG. 6C, the surface mode liquid crystal cell 35 is shown in its fully energized state with the relatively maximum voltage electric field $E_2$ being applied thereto to align substantially all of the liquid crystal material 43 with respect to the field. As a result, light 50 transmitted through the cell 35 will only experience the ordinary index of refraction of the liquid crystal material and will not experience birefringence; therefore, the birefringence term and the thickness of the birefringent layer term of Equation 1 are zero or near zero. Accordingly, the result of Equation 1 goes to zero, and there will be no retardation of the plane polarized light 50 incident on the cell 35 as such light is transmitted therethrough. Therefore, a substantial amount of light directed from the cell 35 to the analyzer 34 will be blocked by the relatively crossed analyzer 34 allowing only an adequate amount for the welder to safely see the welding area, for example, 0.1% transmission, preferably 0.01% transmission, and possibly even less transmission of light relative to the amount of light incident on the welding lens. Such blocking of light is independent of the wavelength of the light.

The just described operation represents the dark state for the lens 31.

It will be appreciated that the magnitude of the electric field $E_2$ is greater than the magnitude of the electric field $E_1$. Therefore, the maximum field is used to drive the lens 31 to the dark state, and, accordingly, the speed of operation will be maximized. Moreover, it will be appreciated that the surface mode liquid crystal cell 35 (especially in combination with the polarizer and analyzer) when in the de-energized or power off mode described with respect to FIG. 6A provides light intensity modulation with respect to wavelength. However, the surface mode liquid crystal cell 35 is used for its light intensity modulation characteristics independent of wavelength in the clear and dark state described operation with respect to FIGS. 6B and 6C.

It also will be appreciated that by varying the voltage of the electric field applied to the surface mode liquid crystal cell 35 between the voltages that provide the clear and clear state and the dark state, there can be obtained a substantially analog variation in the intensity of the transmitted light or analog variation in the shade number of the lens without regard to color. Since the surface mode liquid crystal cell 35 is operated at zero order between the clear and dark states, varying the voltage of the applied electric field will alter the intensity of the light output by the cell 35 independently of color.

As those skilled in the art will appreciate, the foregoing description of operation of the surface mode liquid crystal cell 35 assumes certain optimized circumstances. For example, the axis of polarization of the polarizer 33 and of the analyzer 34 are at least approximately at right angles with respect to each other, and the rub direction of the liquid crystal cell 35 (also referred to as the axis of the surface mode cell 35) and, thus, the de-energized alignment direction of the liquid crystal material 43 therein is at least approximately at 45 degrees with respect to the axes of the polarizer and analyzer so as to provide optimized retardation or wave plate functions. However, those values and/or relationships can be varied, as is known, in which case similar operation will occur, but compensation may have to be provided, e.g, along the lines disclosed in the above-mentioned patents relating to the surface mode liquid crystal cell invention and as is elsewhere described herein and in other literature. Further, the foregoing description presumes that all liquid crystal aligns in the cell 35 either parallel to the surfaces or perpendicular to the surfaces (i.e., parallel to the applied field) and that in the presence of the field $E_2$ all liquid crystal 43 aligns with the field. In fact this may not be the case due to certain surface energy, surface connection, and tilt angle considerations in the liquid crystal cell 35. However, as also is disclosed in the above referenced patents, copending U.S. patent applications Ser. No. 07/814, 372, filed Dec. 26, 1991 (now U.S. Pat. No. 5,248,880, issued Sep. 28, 1993), 08/089,265, filed Jul. 9, 1993, the entire disclosures of which are incorporated by reference, below, and in the published literature, compensation for the effects of these realities is possible and, in fact, is included in the embodiment which is described below. Nevertheless, it will be appreciated that the principles of the invention envision operation in circumstances without the need for such compensation either in the circumstances of ideal materials or conditions, or where acceptance of a variation in the operation of the lens still provides the desired or adequate optical operational characteristics for a given job.

Figures 7, 8:
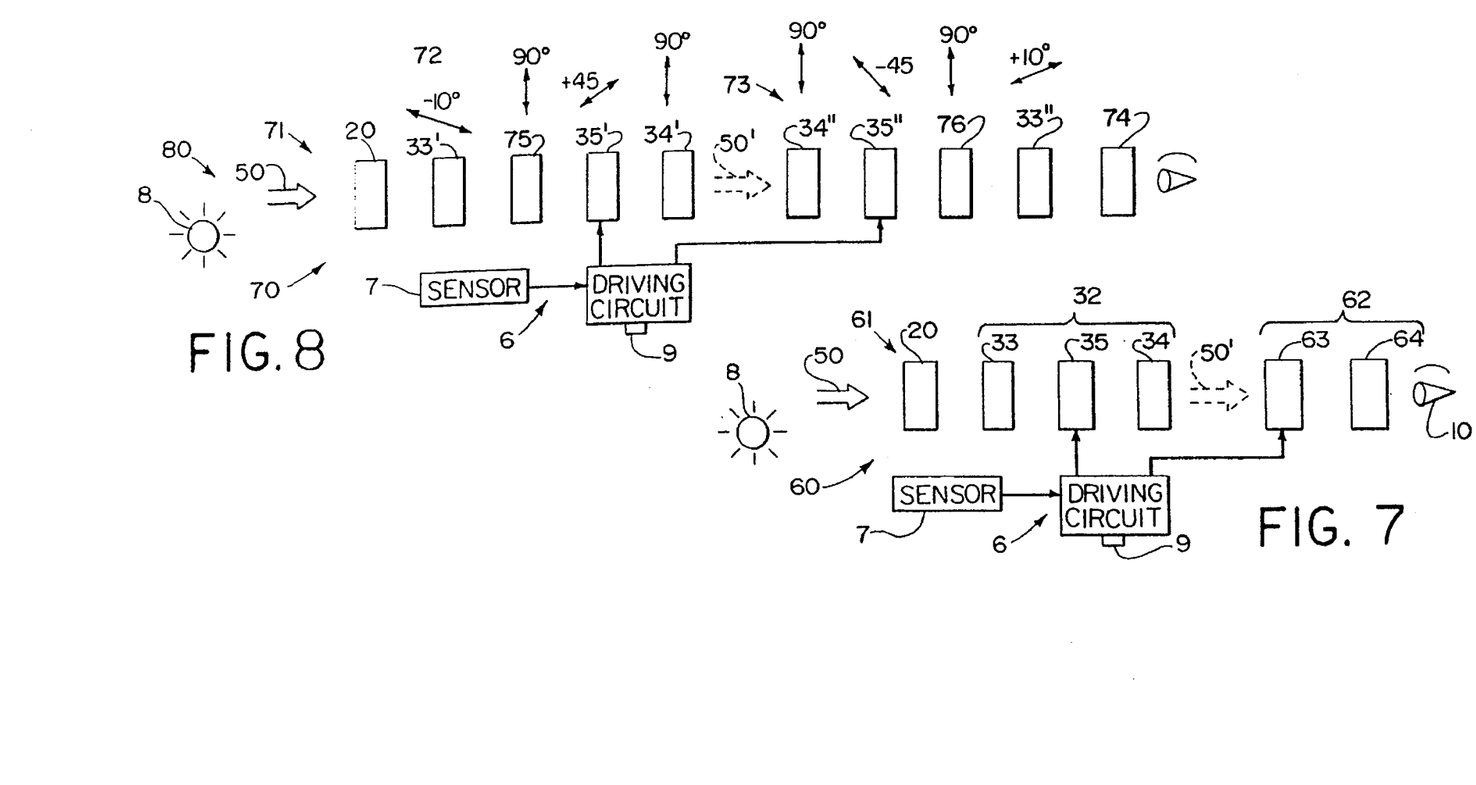
FIG. 7 is a schematic view of an embodiment of the lens of FIG. 2 using two liquid crystal stages and wherein at least one is a surface mode liquid crystal cell.
FIG. 8 is a schematic view of the preferred embodiment of the lens of FIG. 2 using two surface mode liquid crystal devices and a band pass filter.

Multiple Variable Devices Embodiments:

Turning, now, to FIG. 7, a modified embodiment of filter assembly 60 with a welding lens 61 and driving circuit 6 including a sensor 7, is shown. The lens 61 is similar to the lens 31 except that it includes an additional optical stage 62 for further attenuating light, particularly during the dark state. Thus, the lens 61 has three stages, that of the band pass filter 20, that of the variable device 32, and that of the additional optical stage 62.

It is known that polarizers are not perfect optical elements in that the light transmitted by a plane polarizer may include some light that is not polarized in the direction of polarization of the polarizer. Such imperfections therefore may permit some residual leakage of light through the lens 31. Further residual leakage of light through the lens 31 may occur due to the imperfections in the surface mode liquid crystal cell 35 and misalignments of the cell relative to the polarizer and analyzer as well as the reality of alignment characteristics of the liquid crystal in the cell, e.g., tilt angle proximate the surfaces, continuity of alignment between the surface and central areas in FIG. 6B rather than the exemplary abrupt discontinuity between the different aligned portions of liquid crystal material in the cell 35 of FIG. 6B, and actual or near impossibility of aligning all of the liquid crystal at the surfaces in the cell 35 of FIG. 6C.

In the lens 61 the residual light that may leak from the band pass filter 20 and the controllable variable wavelength transmission controlling device 32 in the dark state is represented by 50' (when the lens is in the clear or intermediate state light also is transmitted from the device 32 to the further stage 62). That light is directed to the additional stage 62, which includes a further liquid crystal cell 63 and plane polarizer 64. The further liquid crystal cell 63 may be a surface mode liquid crystal cell, a twisted nematic liquid crystal cell or a dyed liquid crystal cell. Alternatively, the further liquid crystal cell 63 may be another type of device that can be activated selectively to alter effectively the plane of polarization (or to effect retardation) of light transmitted therethrough as a function of a prescribed input, e.g., the electric field supplied by the driving circuit 6.

The additional stage 62 in the lens 61 is intended further to reduce transmission of light through the lens when in the dark state. Depending on the design of the lens 61, the additional stage may or may not contribute to darkening of the lens during the clear and intermediate states. For example, the orientation of the polarizer 64 relative to the orientation of the polarizer 34 may be varied to reduce transmission during clear and/or intermediate states, etc., or to avoid such reduction, e.g., to transmit plane polarized light that is transmitted by the polarizer 34.

The additional stage 62 may be a twisted nematic liquid crystal cell, a dyed liquid crystal cell, or a surface mode liquid crystal cell, or some other device useful selectively to transmit light or to block light transmission, or, possibly in combination with one or more polarizers, if necessary, as is described in U.S. Pat. No. 5,208,688.

Compensated Multiple Stage Surface Mode Liquid Crystal Lens 70:

In FIG. 8 is shown at 70 a modified form of the filter assembly, which includes the filter assembly 60 (of FIG. 7) and also includes two wave plates (designated 75 and 76 in FIG. 8 and described further below) to compensate the surface mode liquid crystal cells 35', 35" for residual birefringence that occurs due to the inability to align all of the liquid crystal material with respect to a maximum applied electric field intended for the dark state. Such inability is due to surface energy and/or anchoring of the liquid crystal material at the respective surfaces of the cell plates. Alternatively, it may be possible to align substantially all or even all (in an ideal circumstance) of the liquid crystal material with respect to a field; but to do so would require a field of greater magnitude than the magnitude of a field that would align less than all but nevertheless an adequate amount of the liquid crystal material. Therefore, use of the wave plates described below will reduce the magnitude of electric field required for effective operation of the filter assembly 70.

Fundamentally, operation of the welding lens 71 of the filter assembly 70 is the same as that described above with respect to the filter assembly 60 and welding lens 61 employing two surface mode liquid crystal cells 35' and 35", as is illustrated in FIG. 7 to achieve the intermediate, clear and dark states. The liquid crystal cells 35' and 35" are analogous to the cells 35 and 63 in FIG. 7; and preferably the liquid crystal cells 35' and 35" are the same. Thus, primed and double primed reference numerals designate respective parts that are the same as or similar to those designated by the same unprimed reference numeral.

The welding lens 71 has three stages, including the band pass filter 20 as the first stage, and two variable devices stages, respectively including a first compensated surface mode liquid crystal stage constituting a controllable variable wavelength transmission controlling device 72, and a second compensated surface mode liquid crystal stage constituting a further controllable variable wavelength transmission controlling device 73. A transparent cover glass 74 at the downstream end of the lens 71 separates the eye 10 from the other parts of the lens for protection of the lens and/or of the eye. Each device 72, 73 preferably is optically the same (although there may be differences, depending on the desired optical result consistent with the disclosure hereof). Each includes a wave plate 75, 76, respectively, which together with a compensating, corresponding or related alignment of the polarizers 33' and 34" provides for compensation for the residual birefringence of the surface mode liquid crystal cells mentioned above.

Briefly, the first controllable variable wavelength transmission controlling device 72 includes a polarizer 33', an analyzer 34', a surface mode liquid crystal cell 35', and the mentioned wave plate 75, which preferably is a quarter wave plate for green light, i.e., it provides quarter wave retardation for green polarized light incident thereon, as is well known. Green light is approximately in the center of the visible light spectrum and it is known to provide wave plate compensation for green light when it is possible that some compensation also is desired for other wavelengths in the visible spectrum as well as green. If desired, though, the wave plate 75 may provide quarter wave retardation for other wavelength(s). To provide the mentioned compensation for residual birefringence and to provide the optical operation described above for the lens 31, for example, alignment of the various elements of the first device 72 relative to a reference direction of "horizontal" is, as follows: The polarizer 33' direction of polarization (transmission axis) is −10 degrees; the axis of the wave plate 75 is 90 degrees; the axis/rub direction of the surface mode liquid crystal cell 35' is 45 degrees; the polarization direction of the polarizer 34' is 90 degrees. Similarly, the alignment of the various elements of the second controllable variable wavelength transmission controlling device 73 relative to the mentioned horizontal direction is, as follows: The polarizer 34" direction of polarization is 90 degrees; the axis/rub direction of the surface mode liquid crystal cell 35" is −45 degrees; the axis of the wave plate 75 is 90 degrees; the polarization direction of the polarizer 33" is 10 degrees. It will be seen that the devices 72, 73 preferably are identical and oppositely positioned for convenience of manufacturing.

Other useful orientations for the components of devices 72, 73 are disclosed in copending U.S. patent applications Ser. No. 07/814,380, now abandoned, and 08/089,265 referred to above and incorporated by reference. As is disclosed in those applications, by changing the relative orientations of the devices 72 and 73 the viewed areas of maximum darkness provided by the lens 71 can be altered or adjusted. As also is described in Ser. No. 07/814,380, now abandoned, quarter wave plates may be used to couple devices 72 and 73. Further, as is disclosed in Ser. No. 08/089,265 the analyzer from one device 72 can serve as the input polarizer to the device 73.

Operation of the filter assembly 70 is similar to the operation of the filter assembly 60. The primary difference is that in the lens 71 the orientation of one polarizer of each device 72, 73 is at plus or minus 10 degrees from the reference axis, and the wave plate in combination with such polarizer arrangement compensates for the residual birefringence of the respective liquid crystal cells 35', 35" in a manner that is described in detail in the above-mentioned patents which relate to surface mode liquid crystal cells. For example, the polarizer 33' plane polarizes the incident light thereon, and the relationship of the axial alignment of the polarizer and the wave plate 75 converts such plane polarized light to elliptically polarized light. The surface mode liquid crystal cell 35', especially when operated in the clear and dark states then tends to convert such light to linearly polarized light which is either blocked or transmitted by the analyzing polarizer 34'.

In the lens 71 of FIG. 8, the band pass filter 20 may be a hot mirror as was described above, or some other band pass filter having the characteristics described herein, the polarizers 33', 34', 33" and 34" cut polarizers, and the wave plates 75, 76 cut wave plates; and the various elements may be adhered together with optical epoxy adhesive material.

Briefly referring to the driving circuit 6 used in the several embodiments hereof, such circuit may be made of conventional parts operative in the manner described herein and in the above incorporated patents and applications. In one embodiment, though, it is preferred that the circuit include a multiple stage voltage level output capability which is operative to provide relatively high voltage and electric field to the surface mode cells 35', 35", for example, of FIG. 8, immediately to cause switching to the dark state to maximize the speed of such switching; after the initiation of such switching, for example, a few microseconds or milliseconds thereafter, the circuit would reduce the voltage, electric field and, thus, the power draw on the circuit battery or other supply to a level that is adequate to maintain the dark state. As was mentioned above, exemplary circuits for carrying out such operation is disclosed in the respective above-identified patent applications.

As was mentioned above, the surface mode liquid crystal cells 35 and 63 in the filter assembly 60 or the surface mode liquid crystal cells 35', 35" in the filter assembly 70 can be tuned to have the same optical, electrical, etc., characteristics, e.g., each having identical transmission curves along the lines of curves 21a, 21b of FIGS. 3 and 4. However, it also is possible that the tuning of such two surface mode liquid crystal cells 35, 63 or 35', 35" can be different. For example, the transmission curve of each may be adjusted to be substantially the same as the curve 21b of FIG. 4 when energized to the clear state. However, the surface mode liquid crystal cells may be tuned so that in the fail state or power off state the transmission curves thereof are different, for example, generally exclusive of each other as is described in U.S. Pat. No. 5,208,688.

The order in which the band pass filter 20 and variable transmission controlling device or devices 21 are placed in the optical path from the source 8 to the eyes 10 is not critical to operation. Preferably, though, the band pass filter 20 is optically upstream of the liquid crystal cell(s) to tend to block infrared energy (and possibly also ultraviolet) therefrom. Preferably, though, when the lens assembly uses two liquid crystal stages, those stages, regardless of the order thereof, should be adjacent each other to optimize use of and cooperation between the plane polarizers thereof, for it is possible that transmission of light through the band pass filter would degrade the polarization of the transmitted light.

From the foregoing, then, it will be appreciated that the present invention provides greater transmission in the clear state of an automatically darkening welding lens system than was heretofore possible. Such greater transmission is possible by using a hot mirror or in any event a band pass filter in the system which is relatively transparent in the visible range of the electromagnetic energy spectrum compared to prior band pass filters which provided relatively substantial filtering even in parts of the visible spectrum. Various embodiments of the invention are described, including wherein fast operation in a drive to dark mode can occur and wherein a warning is provided to indicate power off, power inadequate, failure, etc. Since the clear and dark states of the lens are substantially neutral color, as the band pass filter and the variable optical device both preferably are color independent, the warning being provided by a color function is especially noticeable.

The embodiment described in detail above takes advantage of the characteristics of surface mode liquid crystal cell technology. However, as was mentioned above, the features of the invention may be used in various other types of light control systems, shutters, and the like; several nonlimiting examples include twisted nematic liquid crystal cell, supertwist twisted nematic liquid crystal cell, dyed liquid crystal cell, ferroelectric liquid crystal cell, PLZT, and other technology.

It will be appreciated that although several embodiments have been described herein, the various features disclosed in one embodiment and/or drawing figure, may be employed in the other embodiments and/or drawing figures.

Further, although several embodiments have been illustrated and described, such illustrations and descriptions are intended to be exemplary, and it will be appreciated that the scope of the invention is intended to be limited only by the following claims and the equivalents thereof.

STATEMENT OF INDUSTRIAL APPLICATION

In view of the foregoing, it will be appreciated that the present invention provides apparatus for protecting the eyes of an individual.

I claim:

1. An optical protective lens, comprising a variable optical transmission device responsive to a prescribed input to vary light transmission and light blocking characteristics thereof, and a band pass filter having a relatively wide transmission characteristic in the visible spectrum and a characteristic of substantial blocking of transmission in at least a substantial portion of the infrared spectrum, wherein said band pass filter comprises a hot mirror in combination with a layer of indium in oxide, and wherein said band pass filter has a characteristic of substantial blocking of transmission in the range of greater than about 800 nm to about 2000 nm.

2. The lens of claim 1, wherein said variable optical transmission device comprises a liquid crystal cell.

3. The lens of claim 1, wherein the variable optical transmission device is operative in a drive to dark mode for fast operation.

4. The lens of claim 3, further comprising circuit means for providing electrical input to said variable optical transmission device to cause the device to operate in clear and dark modes, and wherein in the clear mode the variable optical transmission device and band pass filter comprise a neutral filter for visible light.

5. The lens of claim 4, wherein said variable optical transmission device is tuned to provide a warning to indicate a nonoperating condition.

6. The lens of claim 1, wherein further comprising means to provide a warning to indicate a nonoperating condition of the lens.

7. The lens of claim 6, wherein the variable optical transmission device is operative in a drive to dark mode for fast operation.

8. The lens of claim 1, wherein said variable optical transmission device is tuned to provide a warning to indicate a nonoperating condition of the lens.

9. The lens of claim 8, wherein the variable optical transmission device is operative in a drive to dark mode for fast operation.

10. A welding helmet, comprising the lens of claim 1, and means for mounting the lens on the body of a person.

11. The helmet of claim 10, further comprising shield means for protecting the face of a person, and wherein the means for mounting mounts said shield means and lens on the head of a person.

12. A welding helmet, comprising an optical protective lens including a variable optical transmission device responsive to a prescribed input to vary light transmission and light blocking characteristics thereof, and a band pass filter having a relatively wide transmission characteristic in the visible spectrum; wherein said band pass filter comprises a hot mirror in combination with a layer of indium tin oxide to form an optical filter having a characteristic of substantial transmission in at least a substantial portion of the visible spectrum from about 380 nm. to about 700 nm. and of substantial blocking of transmission in at least a substantial portion of the infrared spectrum to about 2000 nm.; wherein said variable optical transmission device is tuned to provide a warning to indicate a nonoperating condition; and wherein the variable optical transmission device is operative in a drive to dark mode for fast operation.

13. The welding helmet of claim 12, further comprising circuit means for providing electrical input to said variable optical transmission device to cause the device to operate in clear and dark modes.

14. A method of operating a welding lens to protect the eyes of a welder, comprising providing the welding lens which includes a band pass filter comprising a hot mirror in combination with a layer of indium tin oxide, and a variable transmission optical device between the eyes of the welder and a source of bright light, using the band pass filter to block transmission of electromagnetic energy in at least a substantial portion of the infrared spectrum in the range of greater than about 800 nm to about 2000 nm while transmitting a substantial portion of light in the visible spectrum, and controlling transmission of light in the visible spectrum by the variable transmission optical device.

15. The method of claim 14, said controlling comprising using the variable transmission optical device to provide substantially clear and substantially dark transmission states.

16. The method of claim 15, said controlling comprising using the variable transmission optical device to produce a third transmission state which indicates at least one of power off, inadequate power or power failure of the welding lens.

17. The method of claim 16, said controlling comprising providing electrical input to the variable transmission optical device to drive the device to clear and to dark states, and automatically detecting welding and providing electrical input to drive the device to the dark state.

* * * * *